United States Patent
Kashimoto

(10) Patent No.: US 6,610,278 B2
(45) Date of Patent: *Aug. 26, 2003

(54) POWDER-BASED SOLID COSMETIC COMPOSITION AND PREPARATION PROCESS THEREOF

(75) Inventor: Akio Kashimoto, Tokyo (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/345,477

(22) Filed: Jul. 1, 1999

(65) Prior Publication Data

US 2002/0028220 A1 Mar. 7, 2002

(30) Foreign Application Priority Data

Jul. 1, 1998 (JP) .......................... 10-186199

(51) Int. Cl.$^7$ ..................... A61K 7/025; A61K 7/035; A61K 31/785; A61K 6/00; A61K 9/16
(52) U.S. Cl. ..................... 424/64; 424/69; 424/401; 424/497; 424/78.17; 424/78.31; 424/78.35
(58) Field of Search ................... 424/401, 497, 424/64, 69, 78.17, 78.31, 78.35

(56) References Cited

U.S. PATENT DOCUMENTS

| | | | | |
|---|---|---|---|---|
| 5,011,680 A | * | 4/1991 | Suzuki et al. ................. | 424/64 |
| 5,958,389 A | * | 9/1999 | Le Bras-Roulier et al. ... | 424/69 |
| 5,972,318 A | * | 10/1999 | Bara ............................ | 424/64 |

FOREIGN PATENT DOCUMENTS

| | | | |
|---|---|---|---|
| JP | 56-108703 | 8/1981 | |
| JP | 57-98205 | 6/1982 | |
| JP | 58-203908 | 11/1983 | |
| JP | 61-69711 | 4/1986 | |
| JP | 1-96110 | 4/1989 | |
| JP | 1-287010 | 11/1989 | |
| JP | 9-301826 | 11/1997 | |
| JP | 09301826 | * 11/1997 | ............ A61K/7/02 |

OTHER PUBLICATIONS

JPO Abstract, JP409301826.*
Encyclopedia of Chemical Technology, vol. 22, p. 120–121, John Wiley & Son Inc. Forth Edition, 1997.*
Partial English Translation of JP 09301826 (2000).*
Patent Abstracts of Japan, vol. 14, No. 63 (C–0685), Feb. 6, 1990, JP 01 287010, Nov. 17, 1989.
Patent Abstracts of Japan, vol. 1997, No. 6, Jun. 30, 1997, JP 09 040529, Feb. 10, 1997.
Patent Abstracts of Japan, vol. 1998, No. 3, Feb. 27, 1998, JP 09 301825, Nov. 25, 1997.
Patent Abstracts of Japan, vol. 1998, No. 4, Mar. 31, 1998, JP 09 328409, Dec. 22, 1997.
Patent Abstracts of Japan, vol. 13, No. 233 (C–601), May 29, 1989, JP 01 042415, Feb. 14, 1989.
Patent Abstracts of Japan, vol. 11, No. 47 (C–403), Feb. 13, 1987, JP 61 210017, Sep. 18, 1986.

* cited by examiner

*Primary Examiner*—Russell Travers
*Assistant Examiner*—Shengjun Wang
(74) *Attorney, Agent, or Firm*—Oblon, Spivak, McClelland, Maier & Neustadt, P.C.

(57) ABSTRACT

A powder-based solid cosmetic composition is provided having a hardness not greater than 75 as measured by an Asker hardness tester type C1L, a porosity of at least 0.4 and an impact resistance of at least 5. A process is also provided for making the powder-based solid cosmetic composition. The composition according to the present invention has excellent skin feel upon use and is not easily broken.

28 Claims, No Drawings

POWDER-BASED SOLID COSMETIC COMPOSITION AND PREPARATION PROCESS THEREOF

This application claims to reign priority of JP 10-186199, filed Jul. 1, 1998.

BACKGROUND OF THE INVENTION

1. Field of the Invention

The present invention relates to a powder-based solid cosmetic composition which has excellent skin feel upon use and is not broken easily by an external force.

2. Description of the Related Art

A powder-based solid cosmetic composition is generally prepared by a press molding method, wherein a raw material composition in a container is solidified by compaction. However, typical powder-based solid cosmetic compositions are poorly bound together, i.e., have poor powder-powder binding power, owing to a relatively small content of an oil component. As a result, high pressure is required to press-mold the solid composition, and the resultant product is necessarily hard and is powdery to the touch.

Generally, the lower the hardness of a powder-based solid cosmetic composition, the lower the powder-powder binding power, and the product is easily broken by an external force.

On the other hand, a solvent method is known which includes mixing a cosmetic composition with a low-boiling-point organic solvent, filling the resulting mixture in the form of a slurry into a container, and then solidifying the composition by removing the solvent (Japanese Patent Application Laid-Open No. Sho 56-108703). Although the solvent method is advantageous because the mixture can be uniformly filled into the container, several problems are associated with the solvent method: shrinkage or cracks appear during drying owing to the evaporation of a large amount of the solvent from the slurry, the filling has a tendency to break, and caking occurs after molding.

SUMMARY OF THE INVENTION

Accordingly, one object of the present invention is to provide a powder based solid cosmetic composition which has excellent skin feel upon use and is resistant to cracks.

The present inventors have found that a powder-based solid cosmetic composition which has excellent skin feel upon use and is resistant to cracks is available by adjusting each of its hardness, porosity and impact resistance to a predetermined value.

One embodiment of the present invention provides a powder-based solid cosmetic composition having a hardness not greater than 75 as measured by an "Asker rubber hardness meter type C1L", a porosity of at least 0.4 and an impact resistance of at least 5.

Another embodiment provides a process for the preparation of the above-described powder-based solid cosmetic composition, which includes mixing powder, a binder including a film-forming polymer having a modulus of elasticity not greater than 200 kg/cm² and a volatile solvent and then solidifying the resulting mixture by volatilizing the volatile solvent.

The present invention provides a powder-based solid cosmetic composition which has excellent skin feel upon use. More particularly, the composition of the present invention has a moisturized feeling, is smooth and permits easy release of powder from the molded product upon use. In addition, the composition of the present invention is free from cracks and is not easily broken by an external force. The powder-based solid cosmetic composition of the present invention is particularly suitable as make-up or a cosmetic such as foundation, face powder, cheek rouge or eye shadow.

BRIEF DESCRIPTION OF THE PREFERRED EMBODIMENTS

Various other objects, features and attendant advantages of the present invention will be more fully appreciated as the same becomes better understood from the following detailed description, which is given for illustration of the invention and is not intended to be limiting unless otherwise specified.

Preferably, from the viewpoint of the feeling upon use and cracks, the powder-based solid cosmetic composition has a hardness not greater than 75, particularly 10 to 75, and more particularly, 20 to 75, as measured by an "ASKER rubber hardness meter type C1L" (trade name), a porosity of at least 0.4, particularly 0.45 to 0.7, and more particularly 0.5 to 0.65, and an impact resistance (as defined below) of at least 5, particularly at least 7, and more particularly at least 8. Among said powder based solid cosmetic compositions are included a foundation having a hardness of 10 to 70, particularly 10 to 65, and an eye shadow having a hardness of 30 to 75, particularly 50 to 75.

The hardness of the molded product is measured directly by an ASKER rubber hardness tester type C1L. In the below-described preparation examples, the hardness was measured using a sample which had been filled in an aluminum pan having a diameter of 54 mm and depth of 4 mm, molded and then dried. The porosity was determined in accordance with the below-described equation based on the measuring results of the weight and volume of the molded product and true density of the powder.

$$\text{Porosity} = 1 - \frac{\text{Weight of molded product}}{\text{True density of the powder}} \times \frac{1}{\text{Volume of molded produc}}$$

In the above formula, the term "molded product" means a cosmetic composition after molding and drying. True density of the powder was measured using "ACCUPUR Model 1330" (trade name: product of Shimadzu Corporation) for the powder mixture used.

Impact resistance was evaluated based on the number of dropping times until a crack appeared in the molded product when it was repeatedly dropped from a height of 50 cm onto a plywood board of 25 mm thick.

In the present invention, it has been found that a powder-based solid cosmetic composition satisfying the above-described conditions exhibits desired performances, the powder-based solid cosmetic composition preferably comprising powder and a film-forming polymer having a modulus of elasticity preferably not greater than 200 kg/cm².

The film-forming polymer to be used in the present invention preferably has a modulus of elasticity not greater than 200 kg/cm², with 1 to 100 kg/cm² being particularly preferred and with 5 to 75 kg/cm² being most particularly preferred. When the modulus of elasticity exceeds 200 kg/cm², the product is inferior in softness or smoothness, leading to a deterioration in the feeling upon use.

In the present invention, the modulus of elasticity was measured as follows:

A 10 wt. % solution or dispersion of each film-forming polymer was weighed in a TEFLON Petri dish having a diameter of 5 cm, and naturally dried for 5 to 10 days. The film so obtained (having a thickness of 0.3 to 0.5 mm) was cut into strips 15 mm long and 5 mm wide and each was used as a sample for the measurement. After allowing a sample to stand at 25° C. and relative humidity of 30% for at least 24 hours, the sample was fixed to a tensile test jig of a dynamic viscoelasticity measuring apparatus ("RHEOSPECTRA DVE-V4" trade name; product of UBM) and measured at an oscillation frequency of 10 Hz and an amplitude of 10 μm.

Preferably, film-forming polymers satisfying the above-described requirement for the modulus of elasticity have a molecular weight of about 10,000 to 1,000,000, more preferably, 15,000 to 900,000, and most preferably, 20,000 to 800,000. Preferred examples include vinyl polymers obtained by the polymerization of at least one moment having a polymerizable double bond, poly(N-acylalkyleneimine)modified silicones and vinyl silicone block polymers. Preferred examples of monomers having a polymerizable double bond include ethylenically unsaturated carboxylic acids such as acrylic acid, methacrylic acid, maleic acid and fumaric acid; unsaturated carboxlic esters such as hydroxyethyl (meth)acrylate and polyethylene glycol mono (meth)acrylate; unsaturated carboxylic amides such as (meth)acrylamide and N-diacetonacrylamide; amino-containing unsaturated carboxylic esters and salts therof such as aminoethyl (meth)acrylate, N,N-dimethylaminoethyl (meth)acrylate, N,N-diethylaminoethyl (meth)acrylate and N,N,N-trimethylaminoethyl (meth)acrylate; aromatic vinyl compounds such as styrene, a-methylstyrene, chlorostyrene and alkylstyrene; acrylic esters and methacrylic esters such as methyl (meth)acrylate, ethyl (meth)acrylate, propyl (meth)acrylate, butyl (meth)acrylate, 2-ethylhexyl (meth)acrylate, t-butyl (meth)acrylate and cyclohexyl (meth) acrylate; vinyl cyanide compounds such as acrylonitrile and methacrylonitrile; vinyl exters such as vinyl acetate; vinyl halides such as vinyl chloride and vinylidene chloride; fluorine monomers such as trifluoroethylmethacrylate, 2,2,3,3-tetrafluoropropylmethacrylate, 2,2,3,3,4,4-hexafluorobutylmethacrylate, perfluorooctylmethacrylate and perfluorooctylacrylate; and silicone macromonomers, represented by the following formulas (1) to (5).

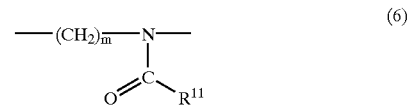

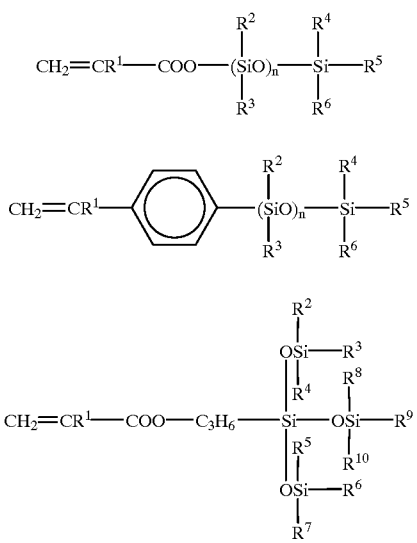

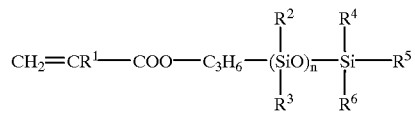

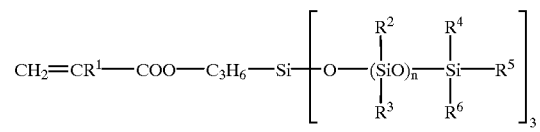

wherein $R^1$ represents a hydrogen atom or a methyl group, $R^2$ to $R^{10}$ each independently represents a $C_1$–$C_6$ alkyl group, $C_1$–$C_6$ alkoxy group or a phenyl group, and n stands for 1 to 500.

As the poly(N-acylalkyleneimine)modified silicone, preferred are those which include a poly(N-acylalkyleneimine) segment composed of recurring units each represented by the following formula (6):

$$-(CH_2)\overline{_m}-N-\underset{\underset{R^{11}}{\overset{\|}{C}}}{\overset{O}{\|}} \qquad (6)$$

wherein $R^{11}$ represents a hydrogen atom, an alkyl group, a cycloalkyl group, an aralkyl group or an aryl group, each having 1 to 22 carbon atoms, and m stands for 2 or 3; and an organopolysiloxane segment having, at an end thereof or as a side chain, the poly(N-acylalkyleneimine) segment composed of the recurring units of the above-described formula (6) bonded through a hetero-atom-containing alkylene group, and contains the poly(N-acylalkyleneimine) segment and organopolysilaxane segment at a weight ratio ranging from 1:50 to 20:1 and has a molecular weight of 10,000 to 500,000, particularly 50,000 to 300,000.

A preferred example of the vinyl-silicone block polymer has, as structural units, a silicone polymer unit represented by the following formula (7):

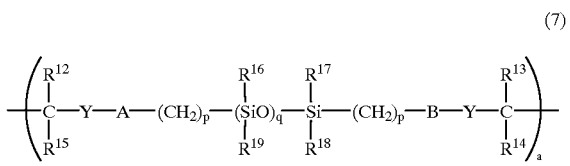

wherein $R^{12}$, $R^{13}$, $R^{14}$ and $R^{15}$ are the same or different and each independently represents a hydrogen atom, a $C_1$–$C_6$ alkyl group or a nitrile group, $R^{16}$, $R^{17}$, $R^{18}$ and $R^{19}$ are the same or different and each independently represents a hydrogen atom, an alkyl group or an aryl group which may be substituted by a halogen atom, Y represents a linear or branched, saturated or unsaturated $C_1$–$C_{10}$ hydrocarbon group which may be substituted by a halogen atom, A represents a —CONH— group or a —COO— group and B represents a —NHCO— group or a —OCO— group, provided that when A represents a —CONH— group, B is a —NHCO— group, and wherein when A represents a —COO— group, B is a —OCO— group, q stands for 0 to 200, p stands for 0 to 6 and a stands for 2 to 300, and a vinyl monomer unit containing no fluorine atom; the total number of silicone monomers constituting the silicone polymer unit of formula (7) preferably falling within a range of from 5 to $10^6$, the total number of the vinyl monomer units preferably falling within a range of from 10 to $10^6$, the sum of the silicon monomers and the vinyl monomers preferably falling within a range of from $10^2$ to $10^6$, and a ratio of the total number of the silicone monomers to the total number of the vinyl monomers falling within a range of from 1/99 to 99/1.

A block copolymer where a silicone polymer represented by the following formula (1a)

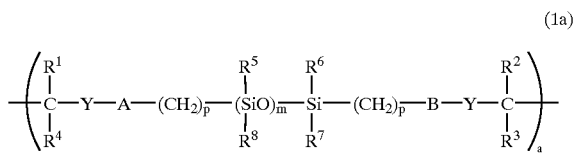

(1a)

In the formula (1a), $R^1$–$R^4$ each is hydrogen atom or a lower alkyl or aryl group having 1–10 carbon (s) and $R^1$–$R^4$ may be same or different. Among the above, methyl group and nitrile group are particularly preferred. $R^5$–$R^8$ each is hydrogen or an alkyl or aryl group which may be substituted with halogen atom and $R^5$–$R^8$ may be same or different. Among the above, methyl group is particularly preferred. Y is a straight-chain or branched-chain and saturated or unsaturated hydrocarbon group having 1–10 or, preferably, 1–6 carbon(s) which may be substituted with halogen atom. Its specific examples are —$CH_2$—, —$(CH_2)_2$—, —$(CH_2)_3$—, —CH $(CH_3)CH_2$—, —$CH_2CH(CH_3)CH_2$—, —$(CH_2)_a$, —$(CH_2)_5$— and —$(CH_2)_6$— and, among them, —$(CH_2)_2$— particularly preferred. A is a —CONH— group or a —COO— group and B is a —NHCO— group or a —OCO— group. Here, when A is a —CONH— group, B is a —NHCO— group while, when A is a —COO— group, B is a —OCO group. m is a number of 0–200 or, preferably, 5–100. When m is more than 200, yield of a vinyl-silicone block copolymer lowers and, in addition, a glass transition temperature of the copolymer becomes too low whereby it is not possible to form a coat having a sufficient strength. p is a number of 0–6 or, preferably, 1–5. a is a number of 2–300 or, preferably, 5–100. When a is 1, a copolymerizing property of the vinyl monomer lowers significantly and, therefore, a case where polymer containing no vinyl monomer or the like may be contaminated as a by-product when a homopolymer of a vinyl monomer containing no silicone skeleton or a degraded product of the formula (1a) is merely recrystallized. On the other hand, when the degree of polymerization is more than 300, the silicone polymer of the formula (1a) becomes a rubber-like substance having a very high viscosity whereby the operating ability in the polymerization lowers such as that its charging becomes difficult or its solubility into a polymerization solvent or into the vinyl monomer used for the copolymerization lowers significantly.

Total numbers of the silicone monomer constituting the silicone polymer represented by the formula (1a) are $5$–$10^6$ or, preferably, $5$–$10^4$ while total numbers of the vinyl monomer are $10$–$10^6$ or, preferably, $10$–$10^9$ and the sum of the total numbers of the silicone monomer and those of the vinyl monomer is $10^2$–$10^6$ or, preferably, $10^2$–$10^4$ where (total numbers of the silicone monomer)/(total numbers of the vinyl monomer) is from 1/99 to 99/1 or, preferably, from 1/99 to 70/30. As such, it is possible to form a coating which has a resistance to sweat and sebum and further has a sufficient strength.

The vinyl monomer may have no fluorine atom at all and its examples are styrene, methacrylic acid or ester thereof, acrylic acid or ester thereof, itaconic acid or ester thereof, vinyl chloride, acrylonitrile, vinyl acetate, ethylene, propylene, butadiene, vinylidene chloride, tetrafluoroethylene and chlorotrifluoroethylene. Among those, methacrylic acid or ester thereof and acrylic acid or ester thereof are preferred.

In the present invention, the vinyl-silicone block copolymer may be manufactured, for example, in such a manner that a polysiloxane amide polymer containing an azo group represented by the formula (2a)

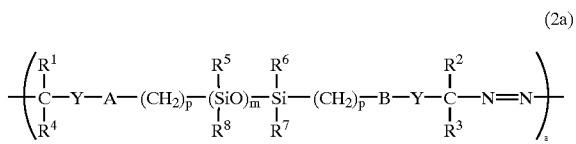

(2a)

(in the formula, $R^1$–$R^8$, Y, A, B, m, p and a are the same as those defined above for formula (1a)) is subjected to a radical copolymerization with a vinyl monomer containing no fluorine atom.

The polysiloxane polymer containing an azo group represented by the formula (2a) (macro azo polymerization initiator) has a specific property that it is easily degraded by heating or irradiation of light together with generation of $N_2$ to give a radical species (a silicone polymer of the formula (1a)) and that, when various vinyl monomers are present at that time, polymerization quickly takes place to produce a block copolymer containing the silicone polymer of the formula (1a).

Accordingly, when heating or light irradiation is carried out in the co-presence of the azo-containing polysiloxane amide polymer of the formula (2a) and the vinyl monomer, the azo-containing polysiloxane polymer of the formula (2a) acts as a polymerization initiator and, at the same time, radical slices having the silicone polymer of the formula (1a) are introduced into the resulting polymer whereupon a vinyl-silicone block copolymer of an $(AB)_n$ type or an ABA type comprising the silicone polymer (A) of the formula (1a) and the vinyl polymer (B) having no fluorine atom can be manufactured efficiently. Although there is no particular need of the polymerization initiator, common radical polymerization initiator such as azobisisobutylonitrile or benzoyl peroxide may be used together.

Radical copolymerization reaction is carried out in the presence or absence of a solvent or a dispersing agent. With regard to the solvent or the dispersing agent, there may be exemplified ethers such as tetrahydrofuran, diethyl ether, dimethoxyethane and dioxane; halogenated hydrocarbons such as methylene chloride, chloroform, carbon tetrachioride and trichlene; hydrocarbons such as petroleum ether, n-hexane, octane, petroleum benzin, benzene, toluene and xylene; alcohols such as methanol, ethanol, isopropanol and tert-butanol; ketones such as acetone, methyl ethyl ketone, methyl isobutyl ketone and cyclohexanone; acetonitrile; water; N,N-dimethylformamide, N,N-dimethylacetamide; dimethyl sulfoxide; cyclic silicones such as octamethyl cyclotetrasiloxane and dodecamethyl cyclohexasiloxane; and chain siloxanes such as dimethylpolysiloxane and methylphenyl polysiloxane and one or more of them may be used. If necessary, an agent for adjusting the degree of polymerization such as n-dodecyl mercaptan may be further added to the reaction system appropriately.

Reaction temperature when the above-mentioned manufacture is carried out by means of heating is appropriately about 30–130° C. usually or, preferably, 50–100° C. and that may be changed as the polymerization goes on. Reaction time is usually about 1–48 hour(s) or, preferably, 1–24 hour(s).

Reaction temperature when the above-mentioned manufacture is carried out by means of irradiation of light is appropriately about 0–60° C. usually or, preferably, 20–50° C. Reaction time is usually about 1 minute to 12 hours or, preferably, 30 minutes to 5 hours. With regard to a light source used for the irradiation of light, a high-voltage mercury lamp may be used for example. With regard to the light for irradiation, it is preferred to be UV light for the polymerization of vinyl monomer which quickly photodegrades the azo-containing polysiloxane polymer.

In the present invention, at least one of the above-exemplified film-forming polymers is preferably used. The film-forming polymer is preferably added in an amount of 0.1 to 15 wt. % based on the whole composition, with 0.5 to 10 wt. % being particularly preferred and 1 to 8 wt % being more preferred.

There is no particular limitation imposed on the powder to be used in the present invention insofar as it is an extender pigment or color pigment ordinarily employed for a cosmetic compositions. Preferred examples include inorganic powder such as silicic acid, silicic anhydride, magnesium silicate, talc, sericite, mica, kaolin, red oxide, clay, bentonite, titanium-coated mica, bismuth oxychioride, zirconium oxide, magnesium oxide, zinc oxide, aluminum oxide, calcium sulfate, barium sulfate, magnesium sulfate, calcium carbonate, magnesium carbonate, iron oxide, ultramarine blue, chromium oxide, chromium hydroxide, calamine and carbon black and complexes thereof organic powder such as polyamide, polyester, polypropylene, polystyrene, polyurethane, vinyl resin, urea resin, phenol resin, fluorine resin, silicon resin, acrylic resin, melamine resin, epoxy resin, polycarbonate resin, divinyl benzene styrene copolymer, silk powder, cellulose, metal salt of a long-chain alkyl phosphoric acid and N-mono(long-chain alkyl)acyl basic amino acid, and mixtures and/or complexes thereof and complexes of the above-exemplified inorganic powder and organic powder.

Preferably, as the powder to be used in the present invention, the above-exemplified ones originally having a hydrophobic surface or having a surface subjected to hydrophobizing treatment can be employed and such powders are preferred because they impart the resulting composition with an improved feeling upon use.

The hydrophobization is preferably conducted using a hydrophobizing agent such as silicone oil, metal salt of fatty acid, alkyl phosphoric acid, alkaline metal salt or amine salt of an alkyl phosphoric acid, N-mono-long-chain (8 to 22 carbon atoms) aliphatic acyl basic amino acid or perfluoroalkyl-containing fluorine compound.

Examples include (A) and (B).

(A) Organopolysiloxane in which, to at least one of silicon atoms at the end or the side-chain of organopolysiloxane segment, poly(N-acylalkyleneimine) comprising the repeating unit represented by the following formula (A-1)

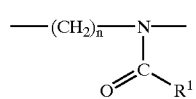
(A-1)

(in the formula, $R^1$ is hydrogen, $C_{1-22}$ alkyl group, cycloalkyl group, aralkyl group or aryl group; and n is 2 or 3) is bonded mediated by an alkylene group containing hetero atom.

In this organopolysiloxane (A-1), it is preferred that the ratio by weight of the said organopolysiloxane segment to the said poly (N-acylalkyleneimine) segment is from 98/2 to 40/60 (more preferably, from 94/6 to 60/40) and that the weight-average molecular weight thereof is from 50,000 to 500,000 (more preferably, from 100,000 to 300,000). When the ratio by weight of organopolysiloxane segment to poly (N-acylalkyleneimine) segment is more than 98/2 or less than 40/60 or when the weight-average molecular weight is less than 50,000, breakage or plastic deformation is apt to take place before the elongation percentage becomes 15% while, when the weight-average molecular weight is more than 500,000, its manufacture is difficult.

With regard to an alkylene group containing hetero atom which mediates the bonding of organopolysiloxane segment to poly(N-acylalkyleneimine), there is exemplified a $C_{2-20}$ alkylene group containing 1 to 3 nitrogen atom (s), oxygen atom(s) and/or sulfur atom(s) and its specific examples are as follows.

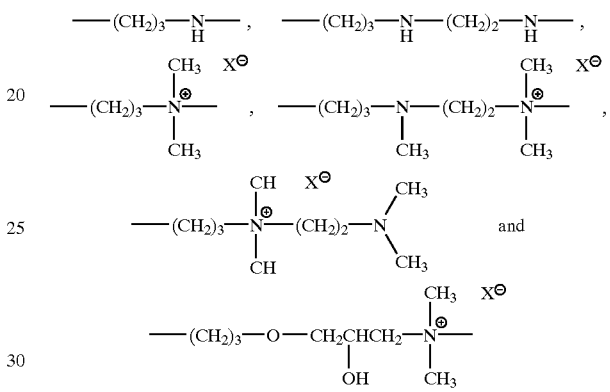

(In the formulae, X⁻ is a counter ion of quatemary ammonium ion.)

With regard to $R^1$, examples of a cycloalkyl group are those having 3 to 6 carbons; examples of an aralkyl group are phenylalkyl and naphthylalkyl; and examples of an aryl group are phenyl, naphthyl and alkyl-substituted phenyl.

The above-mentioned organopolysiloxane (A) may be manufactured, for example, by the reaction of an organopolysiloxane represented by the following formula (A-2)

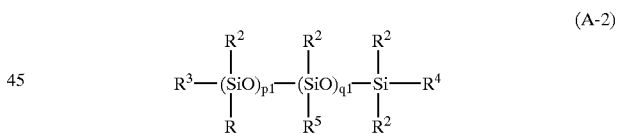
(A-2)

(In the formula, $R^2$s are same or different and each is a $C_{1-22}$ saturated alkyl group or phenyl group; $R^3$ and $R^9$ each is the same group as $R^2$ or a group represented by the following formulae

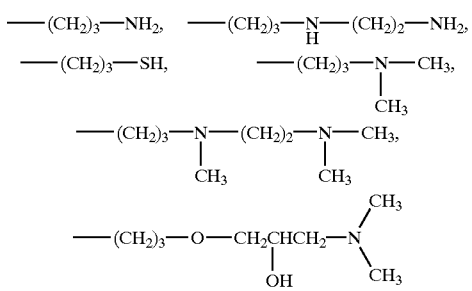

$R^5$ is a group represented by the above-mentioned formulae; $p^1$ is an integer of 100 to 4,000; and $q^1$ is an integer of 1 to 300) with a terminal-reactive poly (N-acylalkyleneimine) which is prepared by a ring-opening polymerization of a cyclic imino ether represented by the following formula (A-3)

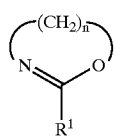
(A-3)

(In the formula, n is 2 or 3 and $R^1$ has the same meaning as defined above).

Here, the ring-opening polymerization of the cyclic imino ether (A-3) is carried out using a compound having a strong electrophilic reactivity such as methyl, ethyl, 3-propenyl or benzyl ester of strong acid such as benzenesulfonic acid, p-toluenesulfonic acid, trifluoromethanesulfonic acid, trifluoroacetic acid or sulfuric acid as an initiator. When, for example, a 2-substituted 2-oxazoline is used as the cyclic imino ether (A-3), there is prepared poly (N-acylethyleneimine) (n=2 in the formula (A-1)) while, when 2-substituted 2-oxazine is used, there is prepared poly (N-acylpropyleneimine) (n=3 in the formula (A-1)).

With regard to a method for connecting the above-mentioned poly (N-acylalkyleneimine) chain to silicone chain, there may be used many means such as reaction for the formation of ester by the condensation of carboxyl group with hydroxyl group; reaction for the formation of amide by the condensation of carboxyl group with amino group; reaction for the formation of secondary, tertiary or quaternary ammonium by the reaction of alkyl halide group with primary, secondary or tertiary amino group; reaction of addition of Si—H group to vinyl group; and reaction for the formation of β-hydroxylamine by epoxy group and amino group and, a method where a terminal-reactive poly (N-acylaikyleneimine) prepared by a cationic ring-opening polymerization of cyclic imino ether is made to react with the organopolysiloxane represented by the formula (A-2) or the modified organopolysiloxane having the above-mentioned substituent on the side chain is simple, convenient and effective.

(B) Organopolysiloxane where, to at least one silicon atom at the end or side chain of organopolysiloxane segment, a group represented by the following formula (B-4)

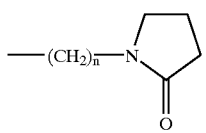
(B-4)

(in the formula, m is an integer of 1 to 8) is bonded.

In this organopolysiloxane (B), it is preferred that numbers of the silicon atom to which the group represented by the formula (B-4) is bonded are from 10 to 90% (more preferably, from 40 to 80%) of the total silicon numbers in a molecular and that its weight-average molecular weight is from 50,000 to 300,000 (more preferably, from 100,000 to 200,000).

Such an organopolysiloxane (B) may be synthesized by, for example, the so-called hydrosilylation reaction where an organohydrogen polysiloxane represented by the following formula (B-5) is used as a precursor and it is made to react with N-alkylenepyrrolidone represented by the formula (B-6). This hydrosilylation reaction may be carried out using a transition metal complex such as platinum chloride at room temperature to 100° C. using a halogen type solvent such as dichioromethane, chloroform or 1,2-dichloroethane or aliphatic ether such as tetrahydrofuran, diisopropyl ether or dibutyl ether as a reaction solvent.

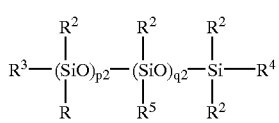
(B-5)

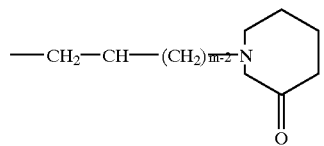
(B-6)

(In the formulae, $p^2$ is an integer of 30 to 3,000; $q^2$ is an integer of 60 to 1,500; and $R^2$, $R^3$, $R^9$ and m have the same meanings as defined already.)

A poly (N-acylalkyleneimine)-modified silicone of a molecular weight of 500–500,000 having a segment of poly (N-acylalkyleneimine) comprising a repeating unit represented by the formula (I-B)

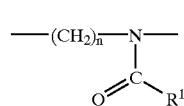
(I-B)

(in the formula, $R_1$ is any of hydrogen atom, an alkyl group having 1–22 carbon(s), a cycloalkyl group, an aralkyl group and an aryl group: and n is 2 or 3) and a segment of organopolysiloxane in a molecule where the poly(N-acylalkyleneimine) segment comprising the repeating unit represented by the above formula (I-B) is bonded to an end and/or a side chain of the segment of organopolysiloxane via a divalent group partially having any of the quaternary ammonium structure selected from the groups represented by the formulae (in the formulae, $X^⊖$ is a counter-ion of the quaternary ammonium salt)

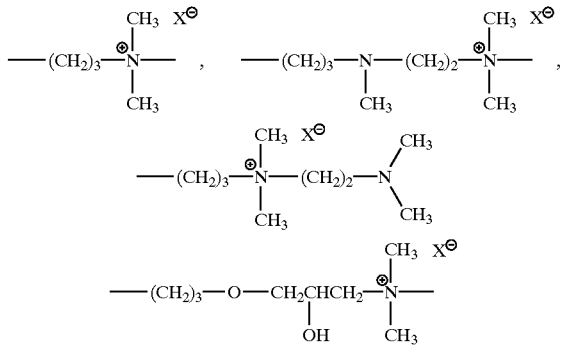

and the ratio by weight of the poly (N-acylalkyleneimine) segment to the organopolysiloxane segment is from 1/20 to 20/1.

The poly(N-acylalkyleneimine)-modified silicone used in the present invention is a modified silicone where a segment of poly (N-acylalkyleneimine) is bonded to the end and/or the side chain of an organopolysiloxane via a specific group and may be synthesized, for example, by the following method. Firstly, a poly (N-acylalkyleneimine) segment comprising the repeating unit represented by the above formula (I-B) is obtained by a ring-opening polymerization of a cyclic imino ether compound represented by the formula (II-B)

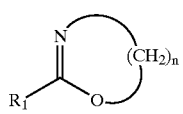

(II-B)

(in the formula, $R_1$ is any of hydrogen atom, an alkyl group having 1–22 carbon(s), a cycloalkyl group, an aralkyl group and an aryl group; and n is 2 or 3). The cyclic iminoether compound represented by the formula (II-B) is 2-oxazolines or 2-oxazines exemplified below. Thus, 2-oxazoline, 2-methyl-2-oxazoline, 2-ethyl-2-oxazoline, 2-propyl-2-oxazoline, 2-butyl-2-oxazoline, 2-pentyl-2-oxazoline, 2-heptyl-2-oxazoline, 2-octyl-2-oxazoline, 2-nonyl-2-oxazoline, 2-decyl-2-oxazoline, 2-undecyl-2-oxazoline, 2-dodecyl-2-oxazoline, 2-tridecyl-2-oxazoline 2-tetradecyl-2-oxazoline, 2-pentadecyl-2-oxazoline, 2-hexadecyl-2-oxazoline, 2-heptadecyl-2-oxazoline, 2-octadecyl-2-oxazoline, 2-nonadecyl-2-oxazoline, 2-eicosyl-2-oxazoline, 2-heneicosyl-2-oxazoline, 2-docosyl-2-oxazoline, 2-benzyl-2-oxazoline, 2-phenyl-2-oxazoline, 2-naphthyl-2-oxazoline, 2-anthryl-2-oxazoline, 2-pyrenyl-2-oxazoline, 2-perylenyl-2-oxazoline, 2-cyclohexyl-2-oxazoline, 2-oxazine, 2-methyl-2-oxazine, 2-ethyl-2-oxazine, 2-propyl-2-oxazine, 2-butyl-2-oxazine, 2-pentyl-2-oxazine, 2-hexyl-2-oxazine, 2-heptyl-2-oxazine, 2-octyl-2-oxazine, 2-nonyl-2-oxazine, 2-decyl-2-oxazine,2-undecyl-2-oxazine, 2-dodecyl-2-oxazine, 2-tridecyl-2-oxazine 2-tetradecyl-2-oxazine, 2-pentadecyl-2-oxazine, 2-hexadecyl-2-oxazine, 2-heptadecyl-2-oxazine, 2-octadecyl-2-oxazine, 2-nonadecyl-2-oxazine, 2-eicosyl-2-oxazine, 2-heneicosyl-2-oxazine, 2-docosyl-2-oxazine, 2-benzyl-2-oxazine, 2-phenyl-2-oxazine, 2-naphthyl-2-oxazine, 2-anthryl-2-oxazine, 2-pyrenyl-2-oxazine, 2-perylenyl-2-oxazine and 2-cyclohexyl-2-oxazine.

With regard to those compounds, only one may be solely used as a monomer for the ring-opening polymerization or two or more thereof may be used jointly therefor. Examples of the polymerization initiator for a ring-opening polymerization of the above-mentioned cyclic imino ethers are alkyl toluenesulfonate, dialkyl sulfate, alkyl trifluoromethanesulfonate and alkyl halide although they are not limitative. Such initiators may be used either solely or jointly.

When the cyclic imino ether compound represented by the above formula (II-B) is subjected to a ring-opening polymerization using such initiators, the poly(N acylalkyleneimine) segment comprising the repeating unit represented by the formula (I-B) is obtained. The said segment may be either a homopolymer chain or a copolymer chain and the said copolymer chain may be either a random copolymer chain or a block copolymer chain. Molecular weight of the above poly (N-acylalkyleneimine) segment is preferably 150–50,000 or, more preferably, 500–10,000. When the molecular weight is less than 150, the property of the poly (N-acylalkyleneimine) is lost while, when it is more than 50,000, its manufactured is difficult and that is not preferred. The poly(N-acylalkyleneimine)-modified silicone of the present invention may be manufactured by the reaction of a polymerization active species produced by a ring-opening polymerization of the cyclic imino ether compound represented by the formula (II-B) with an organopolysiloxane having a functional group which is able to react therewith. The above-mentioned polymerization active species are said to be classified into the types of ion bond species (III-B) and covalent bond species (IV-B) represented by the following formulae

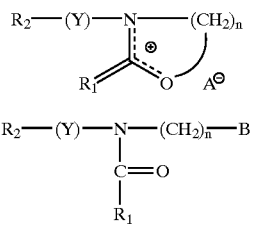

(III-B)

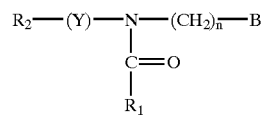

(IV-B)

(in the formulae, Y is a poly(N-acylalkyleneimine) chain; n is an integer of 2 or 3; $R_1$ is hydrogen atom, an alkyl group having 1–22 carbon(s), a cycloalkyl group, an aralkyl group or an aryl group; and $R_2$, A and B are residues for the initiators $R_2$-A or $R_2$-B) (Kobayashi and Saegusa, *Macromolecular Chemistry, Supplement*, Vol. 12, p. 11(1985)). The above-mentioned polymerization active species react with an organopolysiloxane containing a tertiary amino group selected from

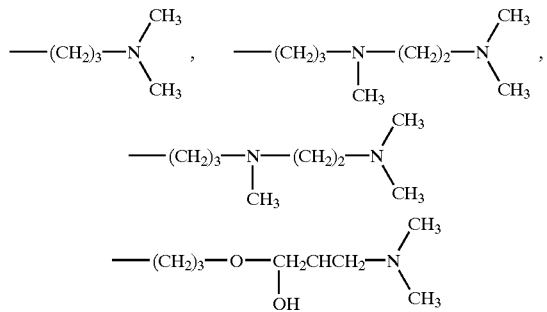

to form a quaternary ammonium salt. Among the organopolysiloxane containing a tertiary amino group used as a material, silicone modified with tertiary amino group at both ends or side chain may be synthesized by a method where an organopolysiloxane having primary or secondary amino groups at both ends or side chain is made into a tertiary substance using alkyl halide such as methyl chloride or propyl bromide or dialkyl sulfate such as dimethyl sulfate; by a method where a silane modifier having a tertiary amine structure such as

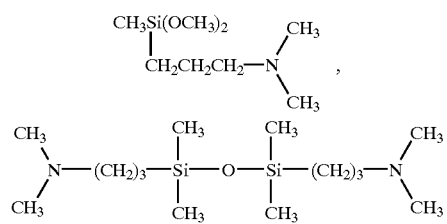

is used and a cyclic silicone such as octamethylcyclotetrasiloxane is polymerized by a conventional method; etc. It is also possible that the above-mentioned polymerization active species is made to react with an organopolysiloxane having primary or secondary amino group and the resulting secondary or tertiary amino group is quatemized by the above-mentioned alkylating agent such as alkyl halide or dialkyl sulfate to give a quaternary ammonium salt. It is further possible to subject the counter-ion to ion-exchange using an ion-exchange resin or the like.

The reaction of an organopolysiloxane containing tertiary amino group or an organopolysiloxane containing primary or secondary amino group with a poly (N-acylalkyleneimine) obtained by a cationic polymerization of cyclic imino ether may be carried out as follows. An initiator is dissolved in a solvent having a low nucleophilicity such as, preferably, one of acetonitrile, valeronitrile, ethyl acetate, dimethylformamide, dimethylacetamide, chloroform, methylene chloride and ethylene chloride or in a mixed solvent with other solvent(s) if necessary and heated at 40–150° C. or, preferably, at 60–100° C. Then the cyclic imino ether represented by the above formula (II-B) is poured thereinto at a time or, when the reaction is vigorous, it is dropped thereinto to carry out the polymerization. Progress of the polymerization can be traced by quantifying the residual amount of the cyclic imino ether which is a monomer using an analytical instruments such as gas chromatography. Even when the cyclic imino ether is consumed and the polymerization is finished, the active species at the growing end still maintains the reactivity. The polymer is not isolated but the said polymer solution is mixed with an organopolysiloxane containing tertiary amino group in a molecule or with an organopolysiloxane containing primary or secondary amino group and made to react under the condition of 5–100° C. or, preferably, at 20–60° C. Although the mixing ratio may be appropriately selected upon request, it is preferred to conduct the reaction at the ratio of 0.1–1.1 molar equivalent(s) of poly(N-acylalkyleneimine) to 1 mole of tertiary amino group or primary or secondary amino group in the organopolysiloxane. When it is less than 0.1 molar equivalent, the degree of modification is little and, therefore, it is difficult to give the property of poly(N-acylalkyleneimine) which is aimed by the present invention while the amount of more than 1.1 molar equivalents is not necessary. When water is present in the reaction system, the reactive end of the poly(N-acylalkyleneimine) reacts whereby the corresponding alcohol and the like are produced and that is not preferred. Thus, it is desired to completely remove the water from the reaction system. Accordingly, it is desired that, even during the reaction, the atmosphere is inert gas such as nitrogen.

For an easier understanding of the poly(N-acylalkyleneimine)-modified silicone, an illustration will be made as hereunder taking the reaction of an organopolysiloxane containing tertiary amino group with the reactive end of poly (N-acylalkyleneimine) as an example.

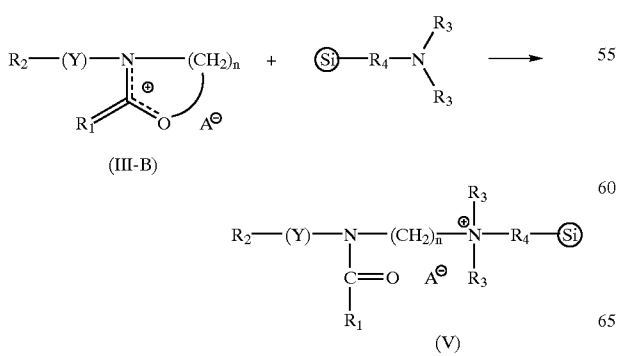

(III-B)

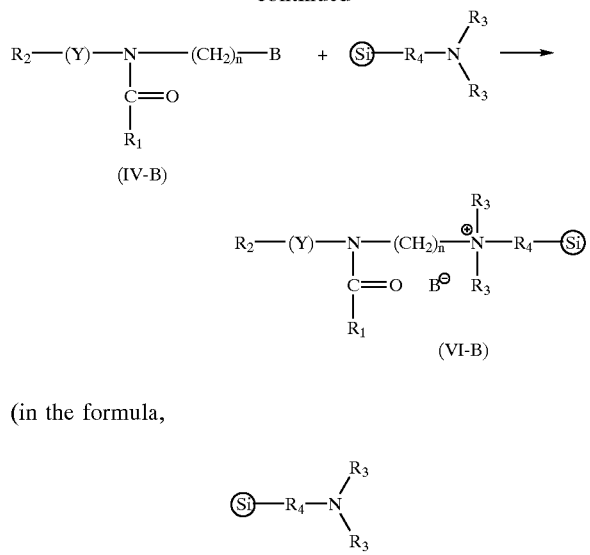

(IV-B)

(VI-B)

(in the formula,

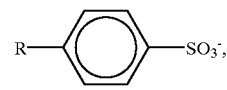

is an organopolysiloxane containing tertiary amino group; $R_3$ is an alkyl or aryl group having 1–18 carbon(s); $R_4$ is an alkylene group; and n, $R_1$, $R_2$, A, B and Y are the same as defined already). With regard to a counter-ion of a quaternary ammonium salt represented by the formulae (V-B) and (VI-B), there is no particular limitation so far as it has a low basicity and its examples are monovalent anions such as $Cl^-$, $Br^-$, $I^-$, $RSO_4^-$, $RSO_3^-$,

R—⟨⟩—$SO_3^-$, $RCO_2^-$ (hereinabove, R is a monovalent aliphatic alkyl group) and lactate ion and a multivalent acid anion such as citric acid, maleic acid, succinic acid, malic acid and sulfosuccinic acid and is able to be ion-exchanged by common methods using an ion exchange resin, etc. As a result of the above-mentioned reaction, it is possible to manufacture the poly(N-acylalkyleneimine)-modified silicone where a poly (N-acylalkyleneimine) molecule chain is added to the end and/or the side chain of the organopolysiloxane via a divalent group containing quaternary ammonium group. Examples of the divalent group partially having a quaternary ammonium structure in the present invention are the groups represented by the following formulae.

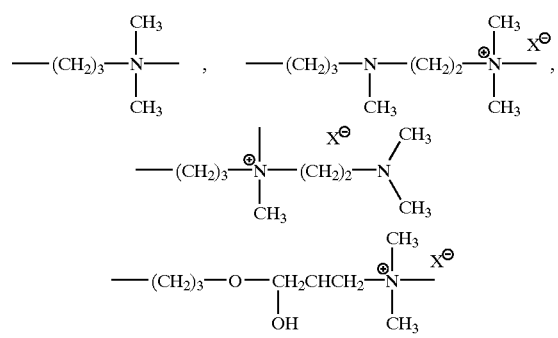

(in the formulae, $X^{\ominus}$ is a counter-ion of the quaternary ammonium salt)

The poly (N-acylalkyleneimine)-modified silicone used shows various states from viscous oil to solid resin depending upon the difference in the type of the organopolysiloxane segment, the type of the poly(N-acylalkyleneimine) segment and combination of both segments. With regard to the ratio by weight of the poly(N-acylalkyleneimine) segment to the organopolysiloxane segment, the range of from 1/20 to 20/1 is able to achieve the characteristic of the present invention and, more preferably, the range is from 1/10 to 5/1. With regard to its molecular weight, the range of 500–500,000 is practical and the more preferred range is from 1,000–100,000. Incidentally, the molecular weight can be determined by a GPC (gel permeation chromatography).

Further, preferred examples of copolymers containing as a hydrophilic segment at least one segment derived from an N-acylalkyleneimine include those containing, in their molecules, at least one segment of a poly(N-acylalkyleneimine), which is formed of recurring units represented by the following formula (1-C):

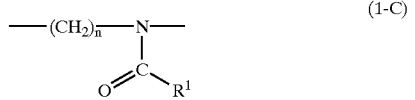

wherein $R^1$ represents a hydrogen atom, an alkyl group having 1 to 22 carbon atoms, a cycloalkyl group, an aralkyl group or an aryl group, and n stands for a value of 2 or 3, and an organopolysiloxane segment, in which the segment of the poly(N-acylalkyleneimine) containing the recurring units represented by the formula (1-C) is bonded via a hetero-atom-containing alkylene group to at least one terminal or side-chain silicon atom of the organopolysiloxane segment. From the standpoint of obtaining stable emulsion products, such poly(N-acylalkyleneimine)-modified silicones preferably can contain the poly (N-acylalkyleneimine) segments and the organopolysiloxane segment at a weight ratio of from 1/50 to 20/1, preferably from 1/40 to 211 and can have a molecular weight of from 500 to 500,000, preferably from 1,000 to 300,000.

Further, illustrative of the cycloalkyl group represented by $R^1$ in the formula (1-C) are those containing 3 to 6 carbon atoms, illustrative of the aralkyl group are phenylalkyl and naphthylalkyl, and illustrative of the aryl group are phenyl, naphthyl and alkyl-substituted phenyl. Examples of the hetero-atom-containing alkylene group which is bonded to at least one terminal or side-chain silicon atom in the organopolysiloxane segment include $C_{2-20}$ alkylene groups containing 1 to 3 nitrogen, oxygen and/or sulfur atoms. Specific examples include groups represented by the following formulas (3-C):

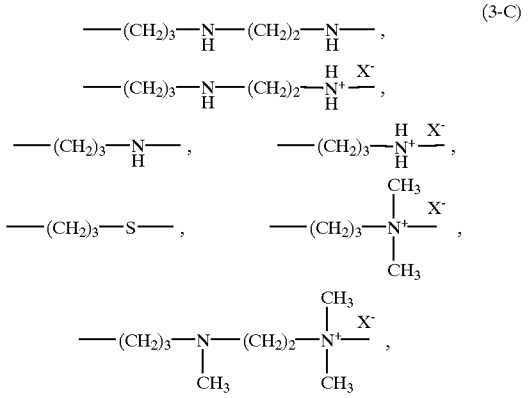

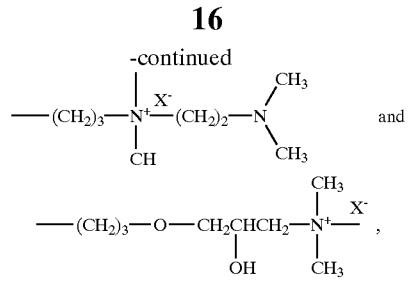

wherein $X^-$ represents a counter ion to a quaternary ammonium sale.

Preferred examples of such poly(N-acylalkyleneimine)-modified silicones include poly(N-formylethyleneimine)-modified silicone, poly(N-acetylethyleneimine)-modified silicone, poly(N-propionylethyleneimine)-modified silicone, poly (N-n-octanoylethyleneimine)-modified silicone, poly(N-n-dodecanoylethyleneimine)modified silicone, poly(N formylpropyleneimine)-modified silicone, poly(N-acetylpropyleneimine)-modified silicone, poly(N-propionylpropylene-imine)-modified silicone, poly (N-n-octanoylepropyleneimine)-modified silicone, and poly(N-n-dodecanoylpropylene-imine)-modified silicone.

The above-described poly(N-acylalkyleneimine)-modified silicones can be obtained by a known process. For example, they can each be synthesized by the following process. First, the segment of the poly(N-acylalkyleneimine) formed of the recurring units represented by the formula (1) can be obtained by subjecting, to ring-opening polymerization, a cyclic imino ether compound represented by the following formula (14-C):

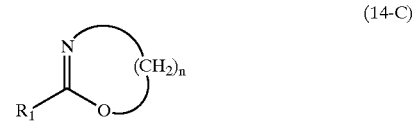

wherein $R^1$ represents a hydrogen atom or a $C_{1-22}$ alkyl, cycloalkyl, aralkyl or aryl group, and n stands for 2 or 3. The cyclic imino ether compound represented by the formula (14-C) can be a 2-oxazoline or 2-oxazine such as that to be exemplified below. Namely, illustrative of the cyclic imino ether compound are 2-oxazoline, 2-methyl-2-oxazoline, 2-ethyl-2-oxazoline, 2-propyl-2-oxazoline, 2-butyl-2-oxazoline, 2-phenyl-2-oxazoline, 2-heptyl-2-oxazoline, 2-octyl-2-oxa-zoline, 2-nonyl-2-oxazoline, 2-decyl-2-oxazoline, 2-undecyl-2-oxazoline, 2-dodecyl-2-oxazoline, 2-tridecyl-2-ocazoline, 2-tetradecyl-2-oxazoline, 2-perrtadecyl-2-oxazoline, 2-hexadecyl-2-oxazoline, 2-heptadecyl-2-oxazoline, 2-octadecyl-2-oxazoline, 2-nonadecyl-2-oxazoline, 2-eicosyl-2-oxazoline, 2-heneicosyl-2-oxazoline, 2-docosyl-2-oxazolins, 2-benzyl-2-oxazoline, 2-phenyl-2-oxazoline, 2-naphthyl-2-oxazoline, 2-anthryl-2-oxazoline, 2-pyrenyl-2-oxazoline, 2-perylenyl-2-oxazoline, 2-cydohexyl-2-oxazoline, 2-oxazine, 2-methyl-2-oxazine, 2-ethyl-2-oxazine, 2-propyl-2-oxazine, 2-butyl-2-oxazine, 2-phenyl-2-oxazine, 2-hexyl-2-oxazine, 2-heptyl-2-oxazine, 2-octyl-2-oxazine, 2-nonyl-2-oxazine, 2-decyl-2-oxazine, 2-undecyl-2-oxazine, 2-dodecyl-2-oxazine, 2-tridecyl-2-oxazine, 2-tetradecyl-2-oxazine, 2-pentadecyl-2-oxazine, 2-hexadecyl-2-oxazine, 2-heptadecyl-2-oxazine, 2-octadecyl-2-oxazine, 2-nonadecyl-2-oxazine, 2-eicosyl-2-oxazine, 2-heneicosyl-2-oxazine, 2-docosyl-2-oxazine, 2-benzyl-2-oxazine, 2-phenyl-2-oxazine, 2-naphthyl-2-oxazine, 2-anthryl-2-oxazine, 2-pyrenyl-2-oxazine, 2-perylenyl-2-oxazine, and 2-cydohexyl-2-oxazine.

These compounds can be used either singly or in combination as a monomer or monomers for ring-opening polymerization.

Examples of a polymerization initiator which can be used to subject the above-described cyclic imino ether to ring-opening polymerization include, but are not limited to, alkyl toluenesulfonates, dialkyl sulfates, alkyl trifluoromethanesulfonates, and alkyl halides. These initiators can be used either singly or in combination.

A molecular chain of a poly(N-acylalkyleneimine) can be obtained by subjecting the cyclic imino ether compound represented by the formula (14-C) to ring-opening polymerization while using such an initiator. This molecular chain can be either a homopolymer chain or a copolymer chain, and the copolymer chain can be either a random copolymer chain or a block copolymer chain.

The molecular weight of the molecular chain of the poly(N-acylalkyleneimine) is preferably 150 or higher but 50,000 or lower, more preferably 500 or higher but 10,000 or lower. A molecular weight lower than 150 no longer has properties of the poly (N-acylalkyleneimine), whereas a molecular weight higher than 50,000 leads to difficulty in preparation. Molecular weights outside the above range are therefore not preferred.

The copolymer with one or more segments derived from the N-acylalkyleneimine as hydrophilic segment(s) can be obtained by reacting an active species for polymerization, said species being formed by subjecting the cyclic imino ether represented by the formula (14-C) to ring-opening polymerization, with an organopolysiloxane containing one or more functional groups reactive to the active species.

Illustrative of the functional groups reactive to the active species include primary, secondary or tertiary amino groups, a mercapto group, a hydroxyl group, and carboxylate groups. Of these, an amino group or a mercapto group is preferred. The organopolysiloxane which contains amino groups or mercapto groups in its molecule can preferably have a molecular weight of from 300 to 400,000, with a molecular weight in a range of from 800 to 250,000 being more preferred. The organopolysiloxane can be either linear or branched. As the molecular weight of the organopolysiloxane, a molecular weight lower than 300 is not preferred from the viewpoint of obtaining a stable emulsion product, but a molecular weight higher than 400,000 leads to a gel-like organopolysiloxane which is difficult to react. Accordingly, molecular weights outside the above range are not preferred.

The thus-contained amino or mercapto groups can be introduced into the backbone or the side chains.

The reaction between the organopolysiloxane containing amino or mercapto groups and reactive terminals of the poly(N-acylalkyleneimine) obtained by the cationic polymerization of the cyclic imino ether can be conducted as will be described below.

An initiator is dissolved in a polar solvent, preferably a single solvent such as acetondrile, valeronitrile, dimethylformamide, dimethylacetarnide, chloroform, methylene chloride, ethylene chloride, ethyl acetate or methyl acetate or, if necessary, a mixed solvent with another solvent, and the resultant solution is heated to 40 to 150° C., preferably 60 to 100° C. To the thus-heated solution, the cyclic imino ether represented by the formula (14-C) is poured at once or, if the reaction is violent, is added dropwise, followed by polymerization. The progress of the polymerization can be traced by quantitating the remaining amount of the cyclic imino ether, the monomer, by an analytical instrument such as gas chromatography. Even after the cyclic imino ether has been used up and the polymerization has been completed, the active species at each growing terminal still retains activity. Without isolation, the polymer solution is then mixed with an organopolysiloxane containing amino or mercapto groups in its molecule, followed by a reaction at 5 to 100° C., preferably 20 to 60° C. Although their mixing ratio can be suitably chosen as desired, it is preferred to react the poly(N-acylalkylene-imine) in a proportion of 0.1 to 1.3 mole equivalents per mole of the amino or mercapto groups in the organopolysiloxane. A proportion smaller than 0.1 mole equivalent leads to an unduly small modification degree, thereby making it difficult to impart the properties of the poly(N-acylalkyleneimine) as desired in the present invention. On the other hand, a proportion greater than 1.3 mole equivalents is unnecessary.

By a reaction such as that descried above, a block copolymer or graft copolymer containing poly(N-acylalkyleneimine) segments as segments hydrophilic to the polydimethylsiloxane can be obtained.

In addition, it is also possible to use a copolymer in which a group, which is represented by the following formula (4-C):

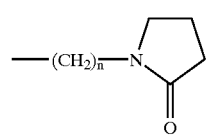

(4-C)

herein m stands for an integer of from 1 to 8, is bonded to at least one terminal or side-chain silicon atom of an organopolysiloxane segment.

In the above copolymer, the number of silicon atoms to which the groups represented by the formula (4-C) are bonded preferably accounts for 10 to 90% (more preferably 40 to 80%) of the total number of silicon atoms in the molecule of said high molecular compound, and the copolymer preferably has a weight average molecular weight of from 1,000 to 500,000 (more preferably 5,000 to 300,000).

A weight average molecular weight of the organopolysiloxane containing the groups (4-C) smaller than 1,000 results in poor emulsion stability, whereas a weight average molecular weight greater than 500,000 leads to difficulty in preparation. If the number of silicon atoms to which the groups represented by the formula (4-C) are bonded is smaller than 10% of the total number of the silicon atoms in the molecule, no sufficient orientation to oil-water interfaces is brought about, resulting in poor emulsion stability. If the former number is greater than 90% of the latter number, the resulting organopolysiloxane shows unduly high water solubility, thereby making it difficult to exhibit emulsifiability.

The organopolysiloxane, which contains such groups (4-C), can be synthesized by a so-called hydrosilylating reaction in which, for example, an organohydrogenpolysiloxane such as that represented by the below-described formula (15-C) is used as a precursor and is reacted with an N-alkylenepyrrolidone such as that represented by the below-described formula (16-C). This hydrosilylating reaction can be conducted at room temperature to 100° C. in the presence of a transition metal complex like hydrogen hexachloro platinate as a catalyst while using, as a reaction solvent, a halogen-containing solvent such as dichloromethane, chloroform or 1,2-dichloroethane or an aliphatic ether such as tetrahydrofuran, diiso-propyl ether or dibutyl ether.

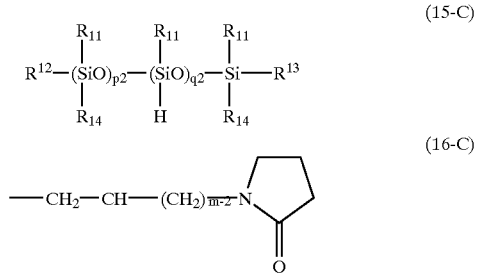

wherein $R^{11}$ is may be the same or different and individually represents a saturated alkyl group or a phenyl group, $R^{12}$, $R^{13}$ and $R^{14}$ individually represents the same group as $R^{11}$s or a group selected from a $C_{1-22}$ saturated alkyl group or a phenyl group, p2 stands for an integer of from 30 to 3,000, q2 stands for an integer of from 60 to 1,500, and m has the same meaning as defined above.

There is no particular limitation on the hydrophobizing method of powder. It may be carried out in a conventional manner. The amount of the hydrophobizing agent is preferably 0.05 to 20 wt. %, and more preferably 2 to 10 wt. % based on the amount of the powder.

As the powder, at least one of the above-exemplified powders can be employed and it is preferably added in an amount of 55 to 99.9 wt. % based on the whole composition, with 65 to 99.9 wt. % being particularly preferred and with 75 to 99.9 wt. % being more preferred.

To the powder-based solid composition of the present invention, an oil component can be preferably added in addition to the above-described components. The oil component is preferably added because it brings about an improvement in a moisturized feeling or adhesion to the skin. Preferable examples of the oil component include solid or semi-solid oils such as Vaseline, lanolin, ceresin, microcrystalline wax, carnauba wax, candelilla wax, higher fatty acid and higher alcohol; fluid oils such as squalane, liquid paraffin, ester oil, diglyceride, triglyceride and silicone oil; and fluorine oil component such as perfluoropolyether, perfluorodecalin and perfluorooctane.

At least one oil component is preferably used, but mixtures of two or more oil components may also be used. The oil component is preferably added in an amount up to about 30 wt. % based on the whole composition, with 20 wt. % or less being particularly preferred and with 15 wt. % or less being more preferred.

Optionally added to the composition of the present invention are a surfactant, antiseptic, antioxidant, coloring matter, thickener, pH regulator, perfume, ultraviolet absorber, humectant, blood circulation accelerator, cooling touch imparting agent, antiperspirant, sterilizer and skin activating agent to any extent so long as the advantages of the present invention are not impaired.

The powder-based solid cosmetic composition of the present invention is preferably prepared, for example, by mixing the powder, a film-forming polymer having a modulus of elasticity not greater than 200 kg/cm² and a volatile solvent, and then solidifying the resulting mixture by evaporating the volatile solvent.

Preferred examples of the volatile solvent include water, low-boiling point alcohols such as ethanol and isopropyl alcohol, hexane, isoparaffin, acetone, ethyl acetate and volatile silicone oil and mixtures thereof. Water and an aqueous solution of an alcohol are particularly preferred.

Upon mixing the powder, film-forming polymer and volatile solvent, it is preferred to add the powder in an amount of 40 to 94.9 wt. %, particularly 50 to 94.4 wt. % the film-forming polymer in an account of 0.1 to 14 wt. % particular 0.5 to 10 wt. % and the volatile solvent in an amount of 5 to 40 wt. %. The mixture is in the form of a slightly wet powder when the volatile solvent is used in an amount of 5 to 40 wt. %. When the amount of the volatile solvent exceeds 40 wt. %, the mixture is in the form of a "slurry" as described in Japanese Patent Application Laid-Open No. Sho 56-108703. In this case, a large amount of the solvent in the slurry is volatilized upon drying and a shrinkage of the solid content, a decrease in the porosity and hardening of the molded product occur, which may presumably causes a problem of cracks. Amounts exceeding the above range are therefore not preferred.

The powder-based solid cosmetic composition of the invention is preferably prepared by filling the mixture of the powder, film-forming polymer and volatile solvent into a container, subjecting it to compression molding and then volatilizing the solvent under suitable conditions (temperature, pressure and time). The conditions for compression molding and solvent volatilization can each be determined as needed, depending on the kind, size and shape of the intended powder-based solid cosmetic composition.

EXAMPLES

Having generally described this invention, a further understanding can be obtained by reference to certain specific examples, which are provided herein for purposes of illustration only and are not intended to be limiting unless otherwise specified.

Preparation Example 1

In a reaction vessel, 150 parts of water, 3 parts of sodium laurylsulfate and 0.5 part of potassium persulfate were charged. The vessel was purged with a nitrogen gas to remove dissolved oxygen. In a dropping funnel, 17 parts of styrene, 33 parts of 2-ethylhexyl acrylate and 2.0 parts of n-dodecylmercaptane were charged. Under stirring, the reaction vessel was heated to 70° C., and the monomers were added dropwise from the dropping funnel over 3 hours. Then the temperature was kept for further 3 hours, followed by removal of the aggregate, whereby an alkyl acrylate copolymer emulsion having a solid content of 45 wt. % was obtained. The emulsion was diluted with water into an emulsion having a solid content of 12 wt. %.

Preparation Example 2

In a reaction vessel, 5 parts of methacrylic acid, 22 parts of methyl methacrylate, 33 parts of n-butyl acrylate, 40 parts of a macroazo polymerization initiator ("VPS0501", trade name; product of Wako Pure Chemical Industries, Ltd., average molecular weight: 30 to 40 thousand) having a polydimethylsiloxane structure, and 200 parts of methyl ethyl ketone were charged. Under stirring at room temperature, the vessel was purged with a nitrogen gas for about one hour, whereby dissolved oxygen was removed. Under stirring the reaction vessel was heated to 80° C., followed by polymerization for 6 hours and further heating for 2 hours at 85° C., whereby a transparent viscous solution was obtained. The resulting solution was diluted with 100 parts of methyl ethyl ketone, neutralized with 5 parts of 1N-NaOH and then added with 600 parts of deionized water. Methyl ethyl ketone was distilled off under reduced pressure. The residue was diluted with deionized water into an emulsion having a solid content of 12 wt. %.

Example 1

A powder-based solid foundation having a composition as shown in Table 1 was produced.

(Preparation Process)

After the powdery components were mixed in a Henschel mixer, the oil component (dimethylpolysiloxane) was added to the resulting mixture. Then, the film-forming polymer was added, followed by mixing.

The resulting mixture was filled in a pan, press-molded and then dried, whereby the powder-based solid foundation was obtained.

The softness, smoothness and release of powders from the molded product were evaluated according to the below-described standards. The impact resistance was evaluated by the number of the dropping times until abnormalities such as cracks appeared when the composition, which had been filled in a pan having a diameter of 54 mm and depth of 4 mm, press-molded under each pressure shown in Table 1 and dried at 50° C. and normal pressure for 3 hours, was dropped repeatedly from a height of 50 cm onto a plywood board of 25 mm thick. Results are shown together in Table 1.

(Evaluation Standards)

A: excellent

B: good

C: slightly inferior

D: inferior.

Clearly, the powder-based solid foundation of the present invention has excellent impact resistance and provides superior feel upon use, compared to the comparative products.

TABLE 1

| Component (wt. %) | Invention products | | | | | | Comparative products | | |
|---|---|---|---|---|---|---|---|---|---|
| | 1 | 2 | 3 | 4 | 5 | 6 | 1 | 2 | 3 |
| Mica treated with silicone (average particle size: 15 μm) | 25.0 | 25.0 | — | — | — | 20.0 | 25.0 | 25.0 | 45.0 |
| Mica treated with silicone (average particle size: 19 μm) | — | — | 60.0 | — | 60.0 | — | — | — | — |
| Talc treated with silicone (average particle size: 10 μm) | 25.0 | 20.0 | — | 30.0 | — | 20.0 | 20.0 | 25.0 | 30.0 |
| Mica treated with fluorine (average particle size: 19 μm) | — | — | — | 30.0 | — | — | — | — | — |
| Spherical silicone resin (average particle size: 12 μm) | 10.0 | 10.0 | — | — | — | 15.0 | 10.0 | 10.0 | 10.0 |
| Spherical silicone resin (average particle size: 4.5 μm) | — | — | — | 12.0 | — | — | — | — | — |
| Spherical PMMA resin powder (average particle size: 12 μm) | — | — | 10.0 | — | — | — | — | — | — |
| Titanium oxide treated with silicone | 5.0 | 5.0 | 5.0 | 5.0 | 5.0 | 5.0 | 5.0 | 5.0 | 5.0 |
| Coloring pigment treated with silicone | 3.0 | 3.0 | 3.0 | 3.0 | 3.0 | 3.0 | 3.0 | 3.0 | 3.0 |
| Dimethylpolysiloxane | 7.0 | 7.0 | 3.0 | — | 2.0 | 7.0 | 7.0 | 7.0 | 7.0 |
| 12 wt. % aqueous dispersion of poly(N-acylalkyleneimine)-modified silicone*1 (modulus of elasticity: 5.3 kg/cm$^2$) | 25.0 | — | 20.0 | 20.0 | — | — | — | — | — |
| 12 wt. % aqueous dispersed emulsion of alkyl acrylate copolymer of Prep. Ex. 1 (modulus of elasticity: 50 kg/cm$^2$) | — | 30.0 | — | — | 30.0 | — | — | — | — |
| 12 wt. % aqueous dispersed emulsion of vinyl silicone block polymer of Prep. Ex. 2 (modulus of elasticity: 5.9 kg/cm$^2$) | — | — | — | — | — | 25.0 | — | — | — |
| 12 wt. % aqueous dispersed emulsion of alkyl acrylate copolymer*2 (modulus of elasticity: 255 kg/cm$^2$) | — | — | — | — | — | — | 30.0 | — | — |
| Purified water | — | — | — | — | — | — | — | 25.0 | — |
| Press molding pressure (kg/cm$^2$) | 2.0 | 1.0 | 3.0 | 5.0 | 2.0 | 2.5 | 1.0 | 5.0 | 900.0 |
| Hardness | 44.0 | 46.5 | 34.0 | 46.2 | 18.0 | 41.0 | 72.0 | 21.0 | 88.0 |
| Porosity | 0.57 | 0.49 | 0.56 | 0.52 | 0.67 | 0.53 | 0.40 | 0.52 | 0.36 |
| Impact resistance | 10 | 15 | 12 | 20 | 20 | 18 | 10 | 1 | 5 |
| Softness | A | B | B | A | A | A | D | D | D |
| Smoothness | A | B | B | B | B | B | D | C | C |
| Easy release of powder from molded product | A | B | B | A | A | B | D | B | B |

*1: the 12 wt. %, aqueous dispersion obtained by dissolving in ethanol a composition as described in Synthesis Example 7 of Japanese Patent Application Laid-Open Hei 10-95705, the entire contents of which are hereby incorporated by reference, followed by solvent substitution.
*2: the 12 wt. % emulsion obtained by diluting "YODOSOL GH-800" (trade name; product of Kanebo NSC) with water.

Example 2

A powder-based solid eye shadow having a composition as shown in Table 2 was produced.
(Preparation process)

The same preparation process as that of Example 1 was performed using 12 wt. % aqueous dispersion of poly(N-acylalkileneimine) modified silicone. Results are shown in Table 2.

Clearly, the powder-based eye shadow of the present invention has excellent impact resistance and provides superior feel upon use, compared to the comparative product.

TABLE 2

| Component (wt. %) | Invention product 7 | Comparative product 4 |
| --- | --- | --- |
| Mica treated with silicone (average particle size: 15 μm) | 15.0 | 15.0 |
| Talc treated with silicone (average particle size: 6 μm) | 15.91 | 15.91 |
| Nylon powder(average particle size: 5 μm) | 5.0 | 5.0 |
| Zinc stearate | 5.0 | 5.0 |
| Paraben | 0.1 | 0.1 |
| Red 202 | 0.01 | 0.01 |
| Yellow 401 | 0.2 | 0.2 |
| Blue 404 | 0.4 | 0.4 |
| Black iron oxide | 0.03 | 0.03 |
| Titanium oxide | 0.05 | 0.05 |
| Mica titanium | 40.0 | 40.0 |
| Bees wax | 2.0 | 2.0 |
| Squalane | 3.0 | 3.0 |
| 2-ethylhexyl palmitate | 3.0 | 3.0 |
| Dimethylpolysiloxane | 2.0 | 2.0 |
| Poly(N-acylalkylneimine)-modified silicone | 8.3 | — |
| Purified water | — | 8.3 |
| Press molding pressure (kg/cm$^2$) | 200 | 200 |
| Hardness | 72 | 71 |
| Porosity | 0.423 | 0.350 |
| Impact resistance | 14 | 4 |

Obviously, numerous modifications and variations of the present invention are possible in light of the above teachings. It is therefore to be understood that within the scope of the appended claims, the invention may be practiced otherwise than as specifically described herein.

This application is based on Japanese patent application 10-186199, filed Jul. 1, 1998, the entire contents of which are hereby incorporated by reference.

What is claimed is:

1. A powder-based solid cosmetic composition prepared by a process comprising:

mixing a composition comprising a powder, a film forming polymer and a volatile solvent to form a mixture; and volatilizing said volatile solvent, wherein said film forming polymer is selected from the group consisting of a vinyl polymer, a poly(N-acylalkyleneimine)modified silicone and a vinyl silicone block copolymer and has a modulus of elasticity of not greater than 200 Kg/cm$^2$, wherein the powder-based solid cosmetic composition has a porosity of at least 0.4, a hardness of not greater than 75 and an impact resistance of at least 5, wherein the impact resistance is defined as the number of dropping times until a crack appears in a molded product of the powder-based solid cosmetic composition, said molded product having a diameter of 54 mm and a thickness of 4 mm after press-molding and drying at 50° C. at normal pressure for 3 hours, when said molded product is dropped from a height of 50 cm onto a plywood board 25 mm thick.

2. The powder-based solid cosmetic composition of claim 1, wherein the film-forming polymer has a modulus of elasticity of 1 to 100 Kg/cm$^2$.

3. The powder-based solid cosmetic composition of claim 1, wherein the film-forming polymer is present in an amount of 0.1 to 15 wt. % based on the weight of the composition.

4. The powder-based solid cosmetic composition of claim 1, wherein the powder is selected from the group consisting of an inorganic powder, an organic powder and a mixture thereof.

5. The powder-based solid cosmetic composition of claim 4, wherein the inorganic powder is selected from the group consisting of silicic acid, silicic anhydride, magnesium silicate, talc, sericite, mica, kaolin, red oxide, clay, bentonite, titanium-coated mica, bismuth oxychloride, zirconium oxide, magnesium oxide, zinc oxide, aluminum oxide, titanium oxide, calcium sulfate, barium sulfate, magnesium sulfate, calcium carbonate, magnesium carbonate, iron oxide, ultramarine blue, chromium oxide, chromium hydroxide, calamine, carbon black and a mixture thereof.

6. The powder-based solid cosmetic composition of claim 4, wherein the organic powder is selected from the group consisting of polyamide, polyester, polypropylene, polystyrene, polyurethane, vinyl resin, urea resin, phenol resin, fluorine resin, silicon resin, acrylic resin, melamine resin, epoxy resin, polycarbonate resin, divinylbenzene styrene copolymer, silk powder, cellulose, a metal salt of a long-chain alkyl phosphoric acid, a N-mono(long-chain alkyl)acyl basic amino acid and a mixture thereof.

7. The powder-based solid cosmetic composition of claim 1, wherein the poly(N-acylalkyleneimine)modified silicone comprises a poly(N-acylalkyleneimine) segment comprising recurring units each represented by the following formula (6):

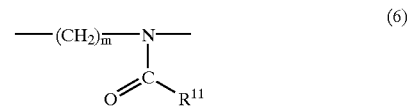

(6)

wherein R$^{11}$ represents a hydrogen atom, a C$_{1-22}$ alkyl group, a cycloalkyl group, an aralkyl group or an aryl group, and m stands for 2 or 3;

and an organopolysiloxane segment having at an end thereof said poly (N-acylalkyleneimine) segment composed of the recurring units of the above-described formula (6) bonded as a side chain or through a hetero-atom-containing alkylene group.

8. The powder-based solid cosmetic composition of claim 7, wherein said poly(N-acylalkyleneimine) segment and said organopolysilaxane segment are present in a weight ratio of from 1:50 to 20:1.

9. The powder-based solid cosmetic composition of claim 1, wherein the mixture is compression molded before volatilizing the volatile solvent.

10. The powder-based solid cosmetic composition of claim 9, wherein the mixture is compression molded at a pressure of 1 to 5 Kg/cm$^2$.

11. The powder-based solid cosmetic composition of claim 1, further comprising mixing an oil to form the mixture.

12. The powder-based solid cosmetic composition of claim 1, wherein the powder-based solid cosmetic composition has a hardness of not greater than 75.

13. The powder-based solid cosmetic composition claimed in claim 1, wherein the powder-based solid cosmetic composition has a porosity of at least 0.4.

14. The powder-based solid cosmetic composition claimed in claim 1, wherein the powder-based solid cosmetic composition has an impact resistance of at least 5,
wherein the impact resistance is defined as the number of dropping times until a crack appears in a molded product of the powder-based solid cosmetic composition, said molded product having a diameter of 54 mm and a thickness of 4 mm after press-molding and drying at 50° C. at normal pressure for 3 hours, when said molded product is dropped from a height of 50 cm onto a plywood board 25 mm thick.

15. The powder-based solid cosmetic composition of claim 1, wherein the volatile solvent is selected from the group consisting of a low boiling alcohol, hexane, isoparaffin, acetone, ethyl acetate, a volatile silicone oil and a mixture thereof.

16. The powder-based solid cosmetic composition of claim 1, wherein the volatile solvent is selected from the group consisting of water and an aqueous solution of an alcohol.

17. The powder-based solid cosmetic composition of claim 1, wherein the powder is present in an amount of from 40 to 94.9% by weight.

18. The powder-based solid cosmetic composition of claim 1, wherein the volatile solvent is present in an amount of from 5 to 40% by weight.

19. The composition according to claim 1, wherein the vinyl polymer is obtained by polymerizing at least one monomer selected from the group consisting of ethylenically unsaturated carboxylic acids, acrylic acid, methacrylic acid, maleic acid and fumaric acid; unsaturated carboxylic esters, hydroxyethyl (meth)acrylate and polyethylene glycol mono (meth)acrylate; unsaturated carboxylic amides, (meth) acrylamide and N-diacetonacrylamide; amino-containing unsaturated carboxylic esters and salts thereof, aminoethyl (meth)acrylate, N,N-dimethylaminoethyl (meth)acrylate, N,N-diethylaminoethyl (meth)acrylate and N,N,N-trimethylaminoethyl(meth)acrylate: aromatic vinyl compounds, styrene, α-methylstyrene, chlorostyrene and alkylstyrene; acrylic esters and methacrylic esters, methyl (meth)acrylate, ethyl (meth)acrylate, propyl (meth)acrylate, butyl (meth)acrylate, 2-ethylhexyl (meth)acrylate, t-butyl (meth)acrylate and cyclohexyl (meth)acrylate; vinyl cyanide compounds, acrylonitrile and methacrylonitrile; vinyl esters, vinyl acetate; vinyl halides, vinyl chloride and vinylidene chloride; fluorine monomers, trifluoroethylmethacrylate, 2,2,3,3-tetrafluoropropylmethacrylate, 2,2,3,3,4,4-hexafluorobutylmethacrylate, perfluorooctylmethacrylate and perfluorooctylacrylate; and silicon macromonomers, represented by the following formulas (1) to (5):

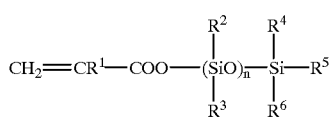

(1)

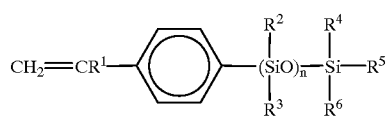

(2)

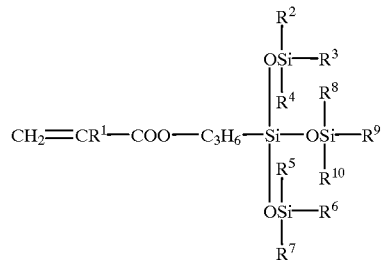

(3)

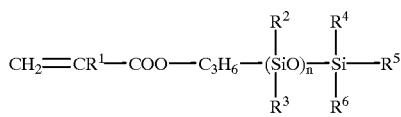

(4)

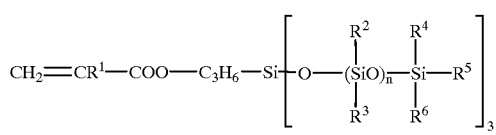

(5)

wherein $R^1$ represents hydrogen atom or a methyl group, $R^2$ to $R^{10}$ each independently represents a lower alkyl group, lower alkoxy group or a phenyl group, and n stands for 1 to 500, and mixtures thereof.

20. The composition according to claim 1, wherein said vinyl-silicone block polymer comprises, as structural units: a silicone polymer unit represented by the following formula (7):

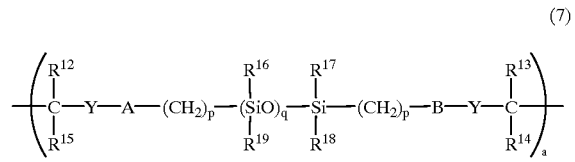

(7)

wherein $R^{12}$, $R^{13}$, $R^{14}$ and $R^{15}$ are the same or different and each independently represents a hydrogen atom, a lower alkyl group or a nitrile group, $R^{16}$, $R^{17}$, $R^{18}$ and $R^{19}$ are the same or different and each independently represents a hydrogen atom, an alkyl group or an aryl group which may be substituted by a halogen atom, Y represents a linear or branched, saturated or unsaturated $C_1$–$C_{10}$ hydrogen group which may be substituted by a halogen atom, A represents a —CONH— group or a —COO— group and B represents a —NHCO— group or a —OCO— group, provided that when A represents a —CONH— group, B is a —NHCO— group, and wherein when A represents a —COO— group, B is a —OCO— group, q stands for 0 to 200, p stands for 0 to 6 and a stands for 2 to 300; and
a vinyl monomer unit containing no fluorine atom.

21. The composition according to claim 20, wherein the total number of silicone monomers constituting the silicone polymer unit of formula (7) is within a range of from 5 to $10^6$.

22. The composition according to claim 20, wherein a ratio of the total number of the silicone monomers to the total number of the vinyl monomers is within a range of from 1/99 to 99/1.

23. A process for preparing a powder-based solid cosmetic composition, having:
a hardness not greater than 75;

a porosity of at least 0.4; and an impact resistance of at least 5, wherein the impact resistance is defined as the number of dropping times until a crack appears in a molded product of the powder-based solid composition said molded product having a diameter of 54 mm and a thickness of 4 mm after press-molding and drying at 50° C. at normal pressure for 3 hours, when a molded product of said composition is repeatedly dropped from a height of 50 cm onto a plywood board 25 mm thick; the process comprising:

mixing a powder, a film-forming polymer having a modulus of elasticity not greater than 200 kg/cm$^2$ and a volatile solvent to obtain a mixture; and then molding the mixture by volatilizing the volatile solvent, wherein the film-forming polymer is a polymer selected from the group consisting of a vinyl polymer, a poly(N-acylalkyleneimine)modified silicone, and vinyl silicone block polymer.

24. The process according to claim 23, wherein the powder, film-forming polymer and volatile solvent are mixed in amounts of 40 to 94.9 wt. %, 0.1 to 14 wt. %, and 5 to 40 wt. %, respectively.

25. The process according to claim 23, wherein the film-forming polymer has a modulus of elasticity of 1 to 100 kg/cm$^2$.

26. The process according to claim 23, wherein the vinyl polymer is obtained by polymerizing at least one monomer selected from the group consisting of ethylenically unsaturated carboxylic acids, acrylic acid, methacrylic acid, maleic acid and fumaric acid; unsaturated carboxylic esters, hydroxyethyl (meth)acrylate and polyethylene glycol mono (meth)acrylate; unsaturated carboxylic amides, (meth) acrylamide and N-diacetonacrylamide; amino-containing unsaturated carboxylic esters and salts thereof, aminoethyl (meth)acrylate, N,N-dimethylaminoethyl (meth)acrylate, N,N-diethylaminoethyl (meth)acrylate and N,N,N-trimethylaminoethyl (meth)acrylate; aromatic vinyl compounds, styrene, α-methylstyrene, chlorostyrene and alkylstyrene; acrylic esters and methacrylic esters, methyl (meth)acrylate, ethyl (meth)acrylate, propyl (meth)acrylate, butyl (meth)acrylate, 2-ethylhexyl (meth)acrylate, t-butyl (meth)acrylate and cyclohexyl (meth)acrylate; vinyl cyanide compounds, acrylonitrile and methacrylonitrile; vinyl esters, vinyl acetate; vinyl halides, vinyl chloride and vinylidene chloride; fluorine monomers, trifluoroethylmethacrylate, 2,2,3,3-tetrafluoropropylmethacrylate, 2,2,3,3,4,4-hexafluorobutylmethacrylate, perfluorooethylmethacrylate and perfluorooctylacrylate; and silicone macromonomers, represented by the following formulas (1) to (5):

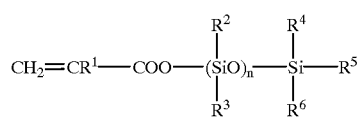

(1)

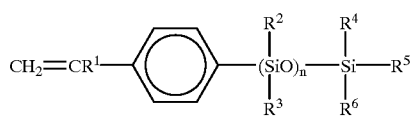

(2)

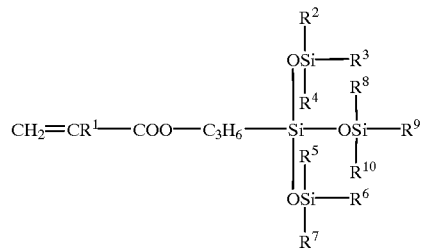

(3)

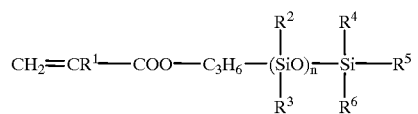

(4)

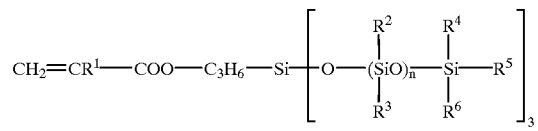

(5)

wherein R$^1$ represents a hydrogen atom or a methyl group, R$^2$ to R$^{10}$ each independently represents a lower alkyl group, lower alkoxy group or a phenyl group, and n stands for 1 to 500, and mixtures thereof.

27. The process according to claim 21, wherein the poly (N-acylalkyleneimine)modified silicone comprises a poly (N-acylalkyleneimine) segment comprising recurring units each represented by the following formula (6):

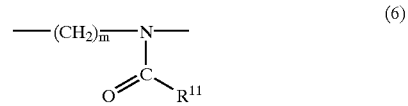

(6)

wherein R$^{11}$ represents a hydrogen atom, an alkyl group, a cycloalkyl group, an aralkyl group or an aryl group, each having 1 to 22 carbon atoms, and m stands for 2 or 3; and an organopolysiloxane segment having at an end thereof said poly(N-acylalkyleneimine) segment composed of the recurring units of the above-described formula (6) bonded as a side chain or through a hetero-atom-containing alkylene group.

28. The process according to claim 21, wherein said vinyl-silicone block polymer comprises, as structural units: a silicone polymer unit represented by the following formula (7):

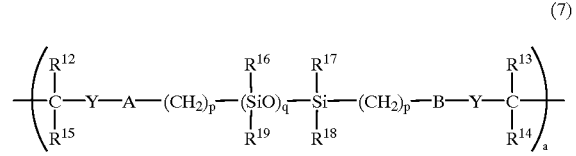

(7)

wherein R$^{12}$, R$^{13}$, R$^{14}$ and R$^{15}$ are the same or different and each independently represents a hydrogen atom, a lower alkyl group or a nitrile group, R$^{16}$, R$^{17}$ R$^{18}$ and R$^{19}$ are the same or different and each independently represents a hydrogen atom, an alkyl group or an aryl group which may be substituted by a halogen atom, Y represents a linear or branched, saturated or unsaturated C$_{1-10}$ hydrocarbon group which may be substituted by a halogen atom, A represents a —CONH— group or a —COO— group and B represents a —NHCO— group or a —OCO— group, provided that when A represents a —CONH— group, B is a —NHCO— group, and wherein when A represents a —COO— group, E is a —OCO— group, q stands for 0 to 200, p stands for 0 to 6 and a stands for 2 to 300; and a vinyl monomer unit containing no fluorine atom.

* * * * *

UNITED STATES PATENT AND TRADEMARK OFFICE
CERTIFICATE OF CORRECTION

PATENT NO.    : 6,610,278 B2
DATED         : August 26, 2003
INVENTOR(S)   : Akio Kashimoto It is certified that error appears in the above-identified patent and that said Letters Patent is hereby corrected as shown below:

<u>Column 28,</u>
Line 30, change "21" to -- 23 --
Line 48, change "21" to -- 23 --

Signed and Sealed this

Eighth Day of June, 2004

JON W. DUDAS
*Acting Director of the United States Patent and Trademark Office*